United States Patent
Teder (10) Patent No.: US 7,847,255 B2
(45) Date of Patent: Dec. 7, 2010

(54) MULTI-MODE RAIN SENSOR

(75) Inventor: Rein S. Teder, Bloomington, MN (US)

(73) Assignee: Pilkington North America, Inc., Toledo, OH (US)

( * ) Notice: Subject to any disclaimer, the term of this patent is extended or adjusted under 35 U.S.C. 154(b) by 495 days.

(21) Appl. No.: 11/901,106

(22) Filed: Sep. 14, 2007

(65) Prior Publication Data

US 2008/0116379 A1 May 22, 2008

Related U.S. Application Data (60) Provisional application No. 60/859,555, filed on Nov. 16, 2006.

(51) Int. Cl.
*G01J 5/08* (2006.01)
(52) U.S. Cl. .................................... 250/341.8
(58) Field of Classification Search ............... 250/341.1, 250/341.7, 341.8, 345
See application file for complete search history.

(56) References Cited

U.S. PATENT DOCUMENTS

| | | |
|---|---|---|
| 5,059,877 A | 10/1991 | Teder |
| 5,414,257 A | 5/1995 | Stanton |
| 5,898,183 A | 4/1999 | Teder |
| 6,232,603 B1 | 5/2001 | Nelson |
| 6,311,005 B1 | 10/2001 | Pientka et al. |
| 7,230,260 B1 | 6/2007 | Tarui |
| 7,236,249 B1 | 6/2007 | Michenfelder et al. |
| 2004/0144911 A1* | 7/2004 | Stam et al. ............. 250/208.1 |
| 2006/0043322 A1 | 3/2006 | Ishikawa et al. |
| 2006/0076477 A1 | 4/2006 | Ishikawa et al. |
| 2006/0076524 A1 | 4/2006 | Yoshigoe et al. |

FOREIGN PATENT DOCUMENTS

EP        1433676 A2 *  6/2004

* cited by examiner

*Primary Examiner*—David P Porta
*Assistant Examiner*—David S Baker
(74) *Attorney, Agent, or Firm*—Marshall & Melhorn, LLC (57) ABSTRACT

The present invention relates to a rain sensor that adaptively functions in a variety of different modes when deployed on vehicle windows of different thicknesses and compositions. The arrangement of multiple lens segments and reflecting surfaces in a nonsequential configuration allows utilization of a greater proportion of light rays from the at least two emitters. Further, a greater portion of the light rays emitted by the at least two emitters is captured by the lens segments and reflectors arranged about at least two detectors, and directed to the detectors. Connection to analytical circuitry then allows interpretation of electrical signals, which in turn control, for example, window wiper systems.

19 Claims, 3 Drawing Sheets

MULTI-MODE RAIN SENSOR

RELATED APPLICATION

This application is claiming the benefit, under 35 U.S.C. 119(e), of the provisional application filed Nov. 16, 2006 under 35 U.S.C. 111(b), which was granted Ser. No. 60/859,555. This provisional application is hereby incorporated by reference in its entirety.

BACKGROUND

The present invention relates generally to an optical rain sensor for detecting water on an automotive window, and more particularly, to a rain sensor that is capable of operating efficiently when mounted on glass of varying thickness and composition.

In recent years, it has been increasingly common for motor vehicles to incorporate optical rain sensing wiper control systems that adjust the speed of the wipers in response to the accumulation of water on the outside surface of, for example, the windshield. The rain sensors of such systems typically employ beams of light directed through the windshield at an angle of 45 degrees. The presence of rain or snow on the outside surface of the windshield disrupts the beams, and the optical rain sensor uses that effect to determine an appropriate speed for the vehicle wipers. A practical implementation of such a system was taught by Teder in U.S. Pat. No. 5,059,877, and the teachings thereof are incorporated herein by reference.

An important factor in the success of a commercial rain sensor is the optical configuration of the sensor. Specifically, the sensor should efficiently couple rays into a vehicle window, and should yield a large sensed area. The sensor should require few opto-electronic devices in order to implement the required sensed area, and to keep the size small and the cost low. Additionally, it is desirable that the rain sensor be compatible with the windows of passenger cars, as well as the windows of larger trucks, recreational vehicles, and other specialty vehicles. Such windows are constructed with a variety of thicknesses and constructions, resulting in different infrared transmittances of the subject structures.

The rain sensor taught in U.S. Pat. No. 5,898,183 to Teder shows that a rain sensor may be made in a very compact and inexpensive form, and yet still operate in a highly efficient manner. The rain sensor of the '183 patent features two emitters and two detectors, each mounted on a planar circuit board, and couples high obliquity rays into the windshield. A consequence of the approach of the '183 patent is that the design must be nominally optimized for each different glass thickness on which the sensor is mounted. By using a sufficiently large aperture, good performance of the rain sensor of the '183 patent can be achieved for the range of thicknesses typically used in passenger cars, i.e., between 4 to 6 mm thick. But, if the same configuration is to be used for windshields deployed on, for example, recreational vehicles, which are typically 8 mm thick, the optical design, must be made proportionately larger. This makes for a physically larger rain sensor. A larger rain sensor is more costly, because of the need for more materials, and is less aesthetically pleasing.

A rain sensor for thick windshields may be made more compact if reflecting surfaces are used to fold the beams toward the inside surface of the rain sensor. Such an approach is taught by Stanton in U.S. Pat. No. 5,414,257. This approach is particularly advantageous for thick windshields, where the thickness of the windshield would dictate that the optical devices would be too far apart if implemented with the refractive approach of the '183 patent. However, the approach is less suitable when deployed on a thin windshield, as an optimal design places the emitter and detector so close together as to risk them interfering with one another. The rain sensor of the '257 patent is thus suitable for only a modest range of windshield thicknesses. A common aspect of the aforementioned rain sensors is that they operate in a single mode of operation. That is, the rays from the emitter strike an optical element, are coupled into the glass, deflect off the outside surface, and so on. Optical systems wherein all rays of interest progress from each surface to the next are known in the field of optical engineering as "sequential", or "deterministic." The other major class of optical systems is known as "nonsequential". In nonsequential systems, a ray emanating from a surface may subsequently strike any of several surfaces, depending on the position and direction of the ray. All of the aforementioned rain sensors utilize sequential optical systems. The rays follow this same deterministic sequence, or mode of operation, regardless of whether the sensor is deployed on thin glass or thick. By the nature of this approach, the rain sensor must be optimized for a particular thickness of windshield. If the sensor is placed on a windshield that is much thicker or much thinner than the design optimum, the rays from the emitter do not strike the optical structure that is supposed to guide the rays to the detector. The result is that the rain sensor either functions poorly or ceases to work at all. It would be better if a sensor could operate in a different fashion for different material thicknesses.

U.S. Pat. No. 6,232,603 describes a device for detecting the presence of moisture on an outside surface of a windshield, which device includes an emitter for transmitting energy, a sensor for receiving energy, an energy absorbing member and a controller for monitoring energy.

U.S. Pat. No. 6,311,005 describes a sensor device for determining the degree of wetting and/or soiling of a pane in a motor vehicle. The sensor device is said to detect moisture on the outer side of the pane via an optical beam which is arranged in the area of the pane. The sensor device includes a reflector positioned in the pane, the reflector intended to direct the beam through the pane under conditions of total reflection or reflection at the outer side of the pane and at the reflector. The pane additionally includes a light filter which absorbs a selected wavelength of sunlight. Attenuation of the light is said to be reduced via an optically more absorbent layer of the light filter.

U.S. Pat. No. 7,230,260 describes a raindrop sensor provided on a first surface of a transparent body for sensing water attached to a second surface of the transparent body, the raindrop sensor including a light emitting element, a light guide body, a light receiving element and an abnormality determining device. The functions of these various components is also described.

A further issue with prior art rain sensors is that they are subject to misalignment. It was shown in the '183 patent that a rain sensor may be made with segmented lenses. Such lenses, known also as Fresnel lenses, offer compact size. Like conventional lenses, they share a common focal point and focal power across the surface of, for example, a glass pane. Thus, if the optical device is misaligned, or the mounting of the rain sensor induces too much deviation to the optical path, it may be possible for a significant portion of emitter rays to miss the detector lens. The effect is controllable in the sensor of the '183 patent, but there remains room for improvement.

Conventional surface mount emitters of infrared radiation radiate into a hemisphere, more strongly on-axis, and decreasing off-axis. The strength of the radiation is, generally, decreased by as much as 50% at 60 degrees off-axis, and decreases even more rapidly when greater than 60 degrees off-axis. Thus, surface mount emitters, are typically said to have a 60 degree half-angle, or 120 degree cone angle. This angle, times the surface area of the emitter, may be a thought of as the "extent" of the emitter. Similarly, the sensitivity of a surface mount detector of infrared radiation, for example, a photodiode drops rapidly beyond 60 degrees off-axis, and are usually also specified as having a 120 degree acceptance cone.

These emitter and detector extents are each in three-dimensions. So, in examining the figures of the present application, one must realize that most of the rays emitted from the emitters are not in the plane of the page on which the figures is printed. The emitters additionally radiate into and out of the plane of each page, and in most known rain sensors this radiation is not utilized. Even if an emitter captures light rays over a cone angle of 40 degrees, taken in three dimensions, this in total utilizes only 12% of the available angular extent of the emitter. Similarly, a cone angle of 40 degrees for the detector side, utilizes but 12% of the available acceptance angle of the detector. The mechanical and optical constraints of rain sensor design make it very difficult to utilize a high extent. Even the best of known rain sensors would approach using only 25% of the available extent on either the emitter or detector side optics. More typical extent utilization in rain sensors is well under 10%

The rain sensor disclosed in the '183 patent seeks to use as many of the light rays that emanate from the emitter as possible. Only those rays that are ultimately coupled into the detector are of value in sensing rain. Similarly, it is desirable to use all of the available angles to direct rays into the detector. The product of detector area and angle is known in the field of optical engineering as the "extent" (E) of the detector, and good use of the available extent allows the least expensive detector for the purpose. While the sensor of the '183 patent represented an advance over the art that came before, it will be appreciated that there is room for improvement in the utilization of emitter rays and target extent.

A sensor utilizing multiple passes, or deflections, through the windshield, may readily be constructed for windshields with high infrared transmittance. Most modern passenger car windshields, however, strongly absorb infrared light, rendering the multi-pass approach inoperative. It would be better if a rain sensor could work as a single-pass sensor when deployed on infrared absorbing glass, and still function as a multi-pass sensor when deployed on clear glass which allows transmittance of fairly high percentages of infrared radiation.

SUMMARY OF THE INVENTION

The present invention is a rain sensor which is compatible with vehicle windows having a wide range of thicknesses and compositions. In the subject rain sensor, an optical coupler, into which optical elements are molded, is optically and mechanically coupled to a vehicle window using a suitable coupling method. A housing is detachably mounted to the coupler, and holds a circuit board generally parallel to the window. Electronic components are mounted on the circuit board, along with at least two emitters and two receivers or detectors. Each emitter is disposed to direct rays through the coupler and vehicle window and onto each of the at least two detectors, thus resulting in a minimum of four similar optical paths.

Optical elements including lens surfaces and reflecting surfaces guide the infrared light from each emitter, through the vehicle window, and into each detector. All of these optical elements are preferably molded into a single optical coupler. The optical elements for the detectors are substantially identical to the corresponding elements for the emitters. Each of the at least four optical paths created by the arrangement of emitters and detectors are substantially identical and symmetric about the center of the rain sensor.

To implement each optical path from emitter to detector, a group of optical elements is molded into the coupler above the level of the emitter relative to the circuit board. This group includes a set of lens segments or lenslets that generally gather and collimate a fan of rays from the emitter, and direct them at an angle of about 45 degrees into the window. Additionally, a "folder" structure gathers some rays that would otherwise travel toward the outside of the rain sensor. The folder structure reflects these light rays back toward the inside of the rain sensor, and thus they are available to travel through the window at an angle of about 45 degrees. A symmetric group of lens segments similar to those arranged about the emitter exists in proximity to the detector. In a fashion analogous to the emitter collimator, the group of emitter lens segments focuses rays traveling through the window toward the detector at about 45 degrees. A second folder structure gathers some light rays that would otherwise miss the detector to the outside, and reflects them back toward its corresponding detector.

The present invention will operate in one of three possible modes, depending upon the characteristics of the window upon which it is deployed, particularly the thickness of the window and the level of infrared radiation transmittance of the window. The three modes of operation may generally be referred to as the "collimator to focuser" mode, the "folder to focuser/collimator to folder mode" and the "folder to folder" mode.

When the present invention is deployed on typical automotive windshields, which are 4.0-6.5 mm in thickness and in the range of 17% to 75% transmissive to infrared radiation, the rain sensor operates predominantly in "collimator to focuser" mode. When on thicker windshields suitable for recreational vehicles, which are typically between 6.5 and 9.5 mm thick and 20% to 75% IR transmissive, the present rain sensor invention operates predominantly in "folder to focuser/collimator to folder" mode. When deployed on exceptionally thick windshields of 9.5-12 mm, the present invention operates predominantly in "folder to folder" mode. When deployed on exceptionally thin and transmissive windshields of 4-4.5 mm and >70% IR transmittance, the sensor will further function in an additional mode that may be considered "folder to folder multi-bounce mode."

By changing modes of operation with deployment on differing windows, the present invention allows a single rain sensor to offer exceptional performance, by maximizing the utilization of the extent E, in a wide variety of applications.

BRIEF DESCRIPTION OF THE DRAWINGS

Additional objects, advantages and features of the present invention will become apparent from the following description and appended claims taken in conjunction with the accompanying drawings in which:

DETAILED DESCRIPTION OF THE INVENTION

The rain sensor of the present invention allows a single rain sensor to efficiently detect the amount of moisture on vehicle windows of widely varying thickness, ranging from unusually thin windows, especially windshields, found on, for example, sports cars to exceptionally thick windows found on, for example, farm tractors. Achieving such efficiency, while keeping the physical size of the rain sensor small, and the cost of manufacturing same low, is, generally accomplished by maximizing the "extent" (E) of the detector(s) of light rays which can then utilize a greater fraction of the total amount of the light rays generated by the emitter(s). Deflection and direction of light rays by an assemblage of lenses adjacent the emitter(s) and detector(s) is also part of the present invention.

The amount of infrared (IR) energy transmittance through a window also affects the efficiency of operation of rain sensors, as earlier discussed herein. In order to account for not only variations in IR energy (or radiation) transmittance, as well as variations in glass thickness, requires that a rain sensor be capable of operating in more than one mode, for reasons which will be explained in greater detail hereinafter. The structure of the present rain sensor further allows for greater tolerance in the manufacturing process, as well as expanding the number of acceptable methods of mounting the rain sensor to the vehicle window.

Figure 1:
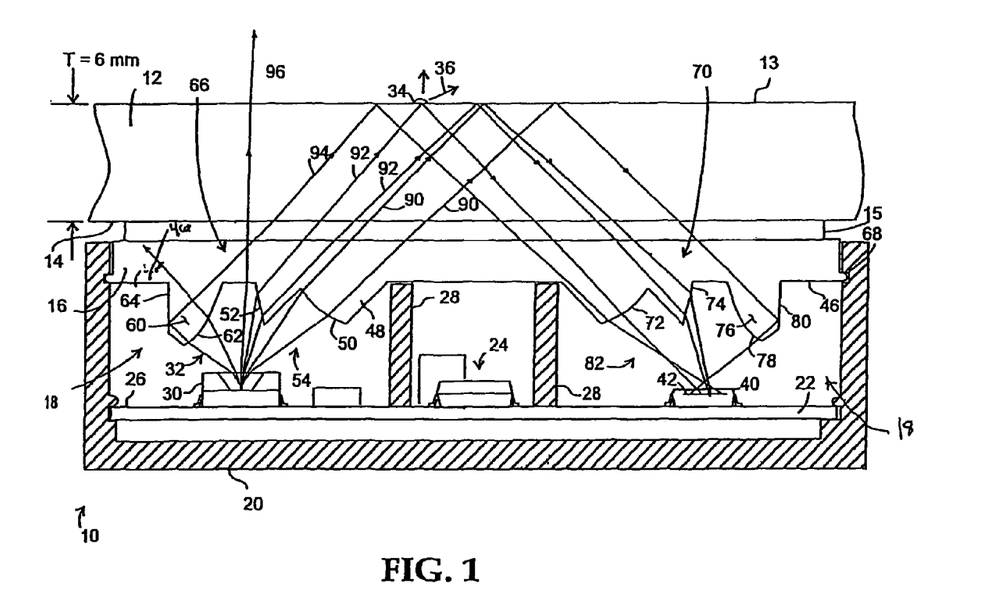
FIG. 1 is a transverse section view of the rain sensor showing the optical path deployed on a windshield having a thickness such as are typically found on passenger cars.

The rain sensor 10 of the present application is shown, generally, in a transverse, cross sectional view in FIG. 1. The rain sensor 10 is mounted upon a vehicle window 12 of thickness T. Window 12 is of conventional laminated construction, comprising two layers of glass with an intervening interlayer of an adhesive plastic material, e.g., polyvinyl butyral. The laminated structure has an outside surface 13 and an inside surface 14. The presence or absence of the plastic interlayer in the laminated structure has no bearing on the invention and is thus omitted for clarity. Rain sensor 10 is preferably mounted to the window 12 using a suitable optically transparent adhesive 15, for example, adhesive tape, glue or other bonding agents may be used. The invention includes a coupler piece 16, into which optical elements, including refracting and reflecting surfaces, are molded. Coupler 16 is typically of an injection-moldable material, such as polycarbonate or acrylic plastic. It is contemplated that coupler 16 could be constructed using multiple-shot molding techniques to incorporate ambient light blocking, but this is not necessary to implement the invention and is not shown here. In FIG. 1, the optical elements molded into coupler 16 are shown generally at 18. A housing 20 is detachably affixed to the coupler. Within the housing a planar printed circuit board 22 is mounted generally parallel to windshield 12.

Mounted upon an upper surface 26 of printed circuit board 22 are conventionally affixed electronic components 24. Such components 24 perform the signal processing and control functions required of the rain sensor. Also mounted on upper surface 26 of the planar circuit board is a representative infrared emitter 30. Each such emitter 30 produces rays over a 180 degree hemisphere, in a nominally Lambertian pattern. That is, the intensity is strongest normal to the circuit board 22, and declines with the cosine of the angle to the normal. The emitter 30 may also be implemented as a chip bonded directly to the circuit board 22. Rays from emitter 30 are shown, generally, at 32. Also on upper surface 26 of circuit board 22 and spaced apart from emitter 30, is a representative infrared detector 40. Each such detector receives rays over a 180 degree hemisphere. A photosensitive die 42 within detector 40 acts to form the active area of the detector 40. The detector 40 is preferably, a photodiode, but a phototransistor, photovoltaic cell, or cadmium sulfide photo-resistor may alternatively be used. A portion of housing 20 forms crosstalk-prevention walls 28 that prevent emitter rays 32 from directly reaching detector 40 without first passing through coupler 16. A representative rain drop 34 is also shown on the outside surface of the laminated window 12.

Coupler 16 largely consists of a planar substrate, having an inside surface 46. An "on-axis" collimator lens 50 is molded onto the coupler substrate at an angle of nominally 45 degrees to the angle normal to emitter 30. On-axis collimator lens 50 has a convex curvature relative to emitter 30. Other optical elements to be described are similarly also molded into coupler 16. On-axis collimator 50 has the effect of substantially collimating rays 32 from emitter 30. The surface of on-axis collimator lens 50 is nominally spherical. The spherical shape extends into and out of the plane of FIG. 1. As will be examined later, emitter rays 32 are not, however, fully collimated, and thus some light rays are slightly divergent. Put differently, emitter 30 is located slightly to the inside of a focal point of on-axis collimator lens 50.

Also disposed on coupler inside surface 46 is an "above-emitter" collimator lens 52. Above-emitter collimator lens 52 has the effect of substantially collimating rays 32 that are closer to an angle normal to the printed circuit board 22, but slightly less than normal. The above-emitter collimator lens also directs the rays reflected from it to be roughly 45 degrees with respect to normal to printed circuit board 22. The surface of above-emitter collimator lens 52 is nominally toroidal, so that the lens may have a sharper radius of curvature into and out of FIG. 1, and a more gradual radius in the plane of FIG. 1. The toroidal aspect of the lens has the effect of reducing aberration of the light rays, compared with a purely spherical shape. Thus, this lens, as well as others described below, extend into and out of the plane of FIG. 1.

On-axis collimator lens 50 and above-emitter lens 52 together comprise a collimator region 54 that, generally, contains a fan of rays 32 emanating from emitter 30, and on-axis collimator lens 50 and above-emitter collimator lens 52 capture and direct rays 32 to an angle of approximately 45 degrees as they enter window 12. Collimator region 54 is shown implemented as two lens sections, but may alternately be implemented in more sections, including segments into and out of the plane of FIG. 1. Preferably, each of the collimator lens sections is kept slightly divergent. That is, it may be seen that rays 92 splay slightly apart, rather than remaining perfectly parallel, as they would were above-emitter collimator lens 52 a perfect collimator. Such divergence is achieved by placing emitter 30 slightly inside the nominal focal point of above-emitter lens 52. It is contemplated that the entire collimator region 54 could be molded as a single surface, combining on-axis collimator lens 50 and above-emitter lens 52 into a single, larger and deeper surface. This would not be as desirable as the lens segments (50, 52) as shown, because it would make for a more difficult-to-mold part. Also molded onto coupler 16 is an inside-reflector structure or "folder" structure shown generally at 60. This structure has the general effect of partially collimating emitter rays 32 moving toward the outside of the rain sensor as represented by reflector surface 64 and deflecting them at a roughly 45 degree angle toward the inside of the rain sensor represented by surface 46. Such a structure may also be considered a "folder", in that it redirects light rays toward the inside of the rain sensor capturing such rays that would otherwise not be utilized and additionally allowing a more compact optical assembly. Reflecting surfaces are often introduced into, for example, binoculars, to render the optical systems more compact. Such surfaces are typically referred to as "folders" in the field of optical engineering. In particular, emitter folder structure 60 includes an emitter-facing lens surface 62. This convex lens surface 62 partially collimates emitter rays 32, as just described. Also molded into folder structure 60 is a reflector surface 64, generally normal to the coupler substrate. Reflector surface 64 is kept as close to perfectly normal as good injection molding practices permit, with a draft angle of nominally 1 degree. As shown in FIG. 1, rays 32 from the emitter 30 perform a total internal reflection (TIR) off reflector surface 64. The reflecting surface 64 and emitter facing lens 62 are joined by material as required to make folder 60 a contiguous volume.

It will be appreciated that the optical configuration shown in FIG. 1 makes use of of nearly the full fan or 100% of rays 32 emanating from emitter 30. High obliquity rays directed toward the inside of the sensor, for example toward inside surface 46, are coupled into the windshield with only modest deflection. In addition to those rays, however, the rays moving toward the outside of the rain sensor, reflector surface 64 are also coupled into the vehicle window after being re-directed by folder structure 60. The aforementioned optical features, on-axis lens 50, over-emitter lens 52, and folder 60, form a group of emitter optical elements 66. Coupler 16 snaps into housing 20 with rib features 68. Alternatively, clip or screw features may be used to affix the coupler. The top surface of coupler 16 forms an optically transparent bond with adhesive 15, and rays traveling through this bond are essentially undeflected. The adhesive 15 forms a similar optically transparent bond with windshield 12.

Also shown in FIG. 1, a group of receiver optical elements 70 is molded into coupler 16 in proximity to detector 40 the optical elements arranged generally symmetrically. An on-axis receiver lens 72 guides light rays moving out of window 12 toward the detector 40 at an angle of approximately 45 degrees. On-axis receiver lens 72 is preferably of identical shape to on-axis collimator lens 50. Thus, the on-axis receiver lens 72 acts as a receiver and focuser lens, gathering a "column" of rays into a ray "pencil" that focuses to a finite-sized spot upon detector die 42. The detector die is large enough to permit some degree of tolerance for misalignment of the beams. Directly analogous to the emitter side on-axis lens 50, on-axis receiver lens 72 accepts a fan of rays that is slightly convergent. That is, the detector die 42 is located slightly inside a focal point of an-axis receiver lens 72. This has the effect of accepting a wider fan of rays than it would if the detector die 42 were located precisely at the focal point. Thus deployed, it can be seen that optical elements 70 for the detector 40 are identical to the corresponding elements for the emitter optical elements 66.

Also included in the group of detector optical structures 70 is an above-detector receiver lens 74. Above-detector lens 74 gathers the column of rays traveling at 45 degrees but generally above and slightly inside detector 40, focusing them to a spot on detector die 42. Further included in detector optical structures 70 is a receiver folder structure 76, deployed to focus rays that are traveling at about 45 degrees within windshield 12, and near the outside of the rain sensor, e.g., surface 46, and reflect them back to the detector die surface 42. Receiver folder structure 76 comprises a convex detector-facing lens 78, a receiver side inside-reflecting surface 80, and material to make the structure a contiguous volume. All of the receiver side group 70 optical elements surfaces are preferably of a shape identical to the emitter-side 66 counterparts. So designed, the coupler may be deployed such that the emitter and detector groups are interchangeable. In a fashion analogous to the emitter optical structure 66, a full fan of rays is directed into the detector group of optical elements 70. Thus, nearly the full extent of the detector target region is utilized: the entire surface area of the detector is illuminated by rain sensing rays, and the rays come from a full splay of angles Also analogous to the emitter side, each set of receiver elements 70 accepts a slightly convergent fan of rays, rather than being perfectly focused. The collection of rays that ultimately strike the detector die 42 forms a receiver ray fan 82.

Still with reference to FIG. 1, rays 32 emanating from emitter 30 may take several paths. "On-axis" rays 90 may be considered those that travel from emitter 30 at nominally close to 45 degrees toward the inside of the rain sensor, and may be, at least, partially collimated by on-axis collimator lens 50. That is, they are on the 45 degree axis, but not the axis normal to the board and the emitter. On axis rays 90 are weaker than those straight out of emitter 30, and thus normal to board 22. This is because of the intensity pattern of the emitter, which shines brightest straight out. On axis rays 90 are already traveling at 45 degrees with respect to board 22, and thus require little deflection from on-axis collimator 50. So, on-axis rays 90 encounter little loss due to surface reflection. The resulting rays 90 are thus still quite strong after coupling into the windshield. Slightly-inside rays 92 are close to the normal of emitter 30, and are thus stronger out of the emitter than are on-axis rays 90. However, above-emitter collimator lens 52 significantly deflects slightly inside rays 92, and the rays thus encounter significant loss due to surface reflection. The effects roughly balance and the slightly-inside rays 92 are intense enough to usefully sense rain. Reflected useful rays 94 initially travel toward the outside of the device, but are deflected back toward the inside of the rain sensor by the emitter reflecting surface 64, ultimately to be directed through window 12 onto detector die 42. Other rays such as 96 emanate from the emitter 40, but miss any of the optical elements of the emitter lens group 66. Such rays do no harm, but are not useful in sensing rain. Other rays, omitted from the figure for clarity, are gathered by the emitter focusing structures, and may undergo one or more reflections, but are not ultimately directed to the detector die 42. Each of the varying paths from emitter 30 to detector 40 may be thought of as "modes". That is, the rain sensor employs several quite different paths for the light rays, and the order of rays passing through the surfaces is not predetermined. Such a system is known in optics as "nonsequential", and the analysis of such systems is more complex than that of a deterministic system. This ability to function in different modes will be examined further later in this document.

Window 12 of FIG. 1 represents a vehicle window 6 mm thick which is, generally, the maximum thickness for windows in typical passenger cars, including laminated structures, such as windshields. T=6 mm may be considered an optimum design thickness for those lenses deployed along the optical path without deflection, e.g., on-axis collimator lens 50 and above-emitter collimator lens 52. That is, coupler 16 is designed such that the following lenses function optimally with, for example, a relatively thick passenger car windshield: on-axis collimator 50, above-emitter collimator 52, on-axis receiver lens 72, and above-detector receiver lens 74.

It will be appreciated that with the lens arrangements as presented, light rays following the path of no single optical axis necessarily travels from emitter to detector without some amount of deflection along its path.

Figure 2:
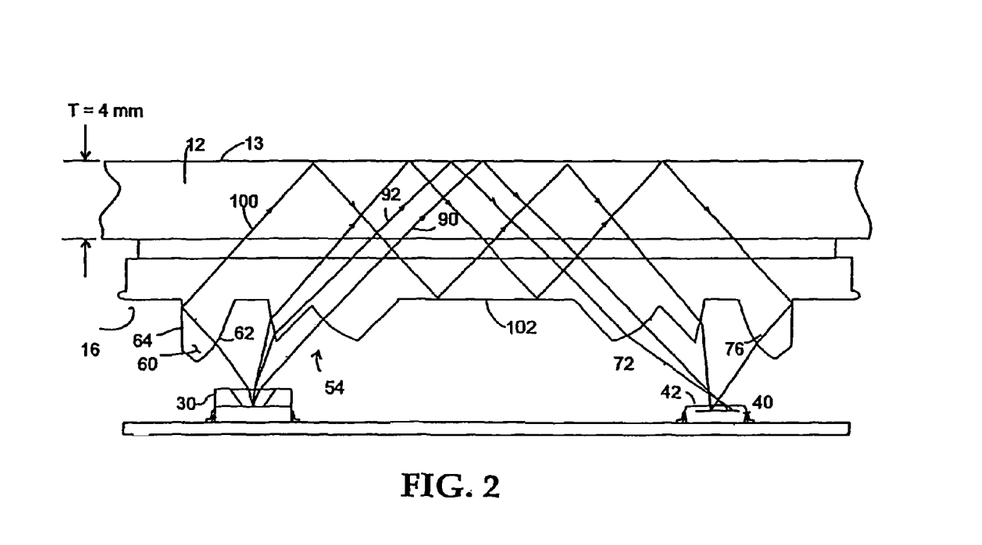
FIG. 2 is a transverse section view of the optical components of the rain sensor when deployed on a thin windshield such as may be found on sports cars.

The optical components of the present invention, deployed on vehicle window 12 of 4 mm thickness T is shown in FIG. 2. Components such as the housing and circuitry are omitted for clarity. A 4 mm thick window such as that of FIG. 2, which is quite thin for, e.g., a windshield, might be used on a sports car, mounted at a very shallow angle for minimum wind resistance and for weight savings. Just as in deployment of the present rain sensor shown in FIG. 1, the coupler 16 deflects on-axis rays 90 and slightly inside rays 92. It can be seen in FIG. 2 that some of the highest obliquity rays are coupled from emitter to detector. Additionally, it may be seen from FIG. 2 that a two-pass, or multi-deflection ray 100 undergoes one or more deflections off a center region 102 of the coupler 16 before being directed to the detector 40. If windshield 12 is relatively transmissive to IR energy, then two-pass ray 100 will be of sufficient amplitude to usefully sense rain. Thus configured, the present invention allows for multi-deflection operation when the glass thickness and IR energy transmittance characteristics are suitable.

Figure 3:
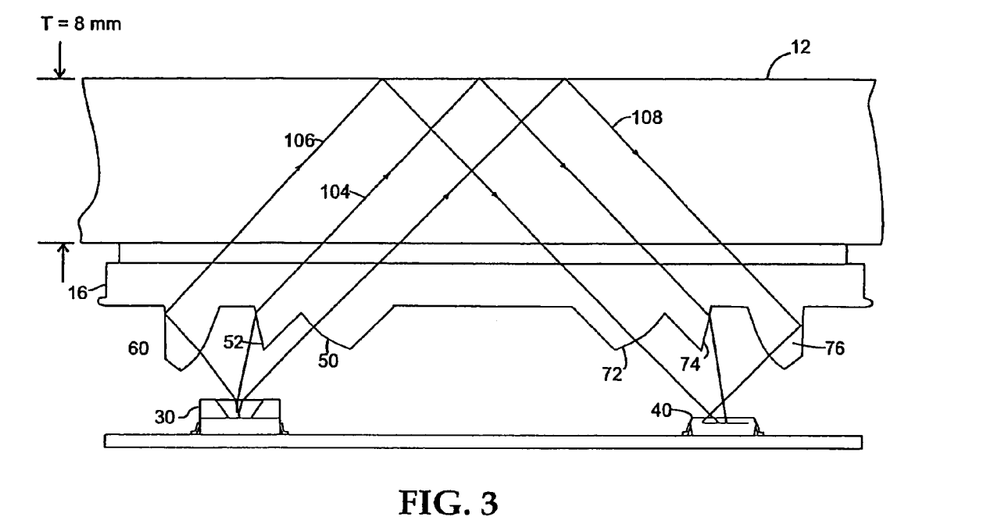
FIG. 3 is a transverse section view of the optical components of the rain sensor when deployed on a thick windshield such as may be found on recreational vehicles.

The present invention is shown in FIG. 3, on vehicle window 12 of nominally T=8 mm. Such a window thickness is typical of a windshield for a recreational vehicle, for example, large, single-piece windshields. In this application a ray 104 travels at an angle slightly off of an angle normal to the emitter 30 to slightly past detector 40, if not redirected. This ray 104 thus traverses both above-emitter collimator lens 52 and above-detector receiver lens 74 which does redirect it into detector 40. Additionally, a ray 106 passes through folder 60 on the emitter 30 side, through windshield 12, and is focused onto the detector 40 by on-axis receiver lens 72. A similar ray 108 traverses through on-axis collimator lens 50, windshield 12, and receiver folder 76 where it is redirected to detector 40. It may be seen that under such conditions the folder structure (60, 72) becomes a more important means of coupling emitter rays to the detector 40. Further, the groups of rays surrounding ray 104, ray 106, and 108 form relatively widely spaced disparate target regions. This increases the sensed area of the windshield 12. The present invention is particularly compact in operation with such a thick windshield, yet offers a very highly sensed area.

Figure 4:
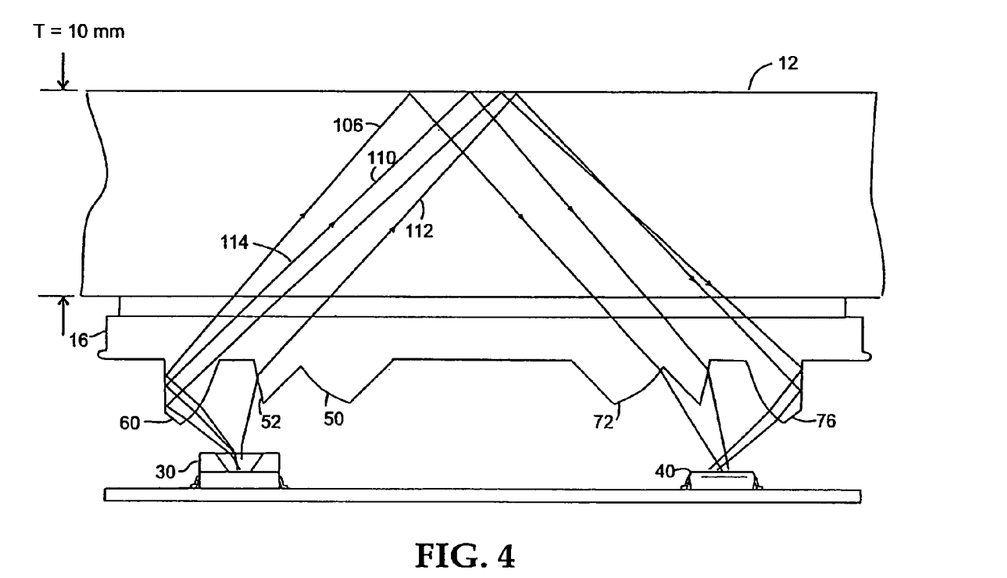
FIG. 4 is a transverse section view of the optical components of the rain sensor when deployed on a very thick windshield such as may be found on tractors.

The present invention is further presented in FIG. 4 on a very thick T=10 mm vehicle window. Windows, for example windshields, may be found in some specialty vehicles that are not used on highways, such as tractors or other farm or constructions equipment. The emitter reflector to on-axis receiver ray 106 exists in a similar fashion to that shown in FIG. 3. Additionally, an emitter ray 110 is redirected by folder 60 to above-detector receiver lens 74. Similarly, ray 112 travels through above-emitter lens 52, through window 12 and is redirected by the detector folder 76 to detector 40. Further, ray 114 travels from emitter side folder 60 to detector side folder 76 where it is redirected to detector 40. The emitter folder to detector folder ray 114 exists on windshields as thick as 12 mm, but such deployments are not illustrated here because the operation of the device is similar to that shown in FIG. 4.

Figure 5:
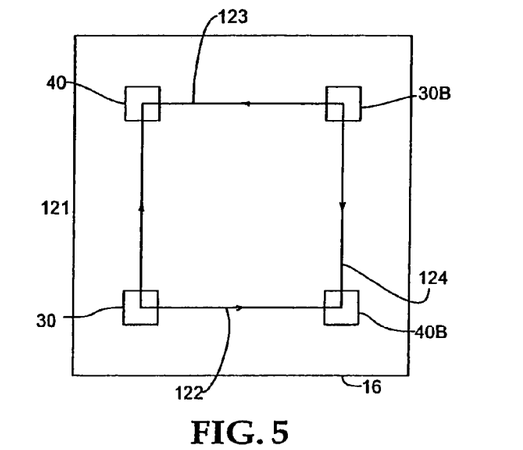
FIG. 5 is a top view presentation showing the relationship of the two emitter and two detectors and connecting optical paths.

The explanation of the optical path herein has thus far been concerned with the optical path from a single emitter to a single detector. In a preferred embodiment of the invention, there are deployed two such emitters and two detectors, forming four such optical paths. The arrangement is shown in a top view in FIG. 5. That is, FIG. 5 shows coupler 16 looking through the windshield, to best illustrate the optical paths of the invention. In this arrangement, emitter 30 shines rays of infrared light onto detector 40, by way of a first optical path 121 through coupler 16. Coupler 16 forms, from the plan view, a square. The optical elements of the path are omitted for clarity. Each of FIGS. 1 through 4 may be taken to be a transverse section along first optical path 121. Additionally, emitter 30 shines rays along a second optical path 122, through coupler 16 to a second detector 40B. The elements of the coupler are shown in a perspective view in FIG. 6. Returning again to FIG. 5, a second emitter 30B is disposed in the corner of coupler 16 opposite emitter 30. Second emitter 30B directs light to detector 40 along a third optical path 123, and onto detector 40. Additionally, second emitter 30B directs light along a third optical path 124 to second detector 40B. Thus configured, each emitter (30, 30B) directs light onto two detectors (40, 40B), making an exceptionally efficient use of optical devices. Thus deployed each of the four optical paths is substantially identical and symmetric about the center of the rain sensor.

Figure 6:
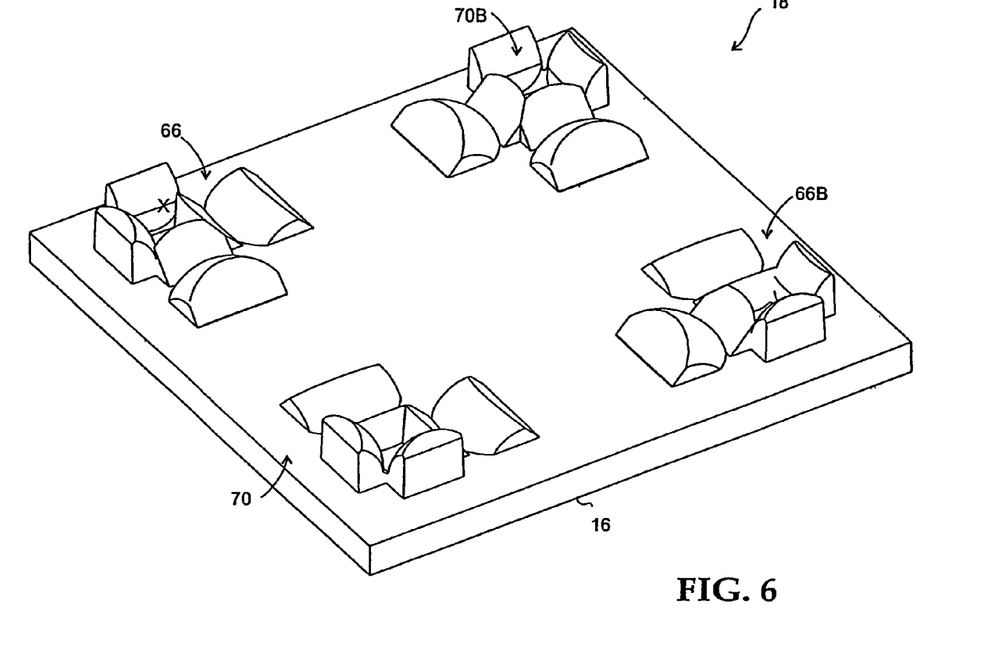
FIG. 6 is a perspective view of the underside of the coupler showing all of the optical surfaces.

FIG. 6 is a perspective view of the underside of the coupler. This figure shows the arrangement of optical elements 18 on the inside surface of coupler 16. A first group of emitter side optical elements 66 is disposed in one corner of the coupler. A second group of emitter side optical elements 66B is disposed in an opposite corner of coupler 16. Similarly, first and second groups (70, 70B) of receiver side optical elements are deployed in the two opposite corners as shown. The location of emitter 30 is shown at "X", just above emitter group 66. Locations of other emitter 30B and the detectors (40, 40B) are similarly located with respect to their corresponding groups of optical elements. It is clear from the figures that regions above the optical elements are densely occupied. Virtually all of the available space surrounding the optoelectronic devices is utilized by structures that gather rays and direct them in a fashion useful for sensing rain. The present rain sensor invention is thus very efficient, making use of a high percentage of available rays.

In operation, the control circuitry (formed with electronic components 24) as shown in FIG. 1, pulses infrared emitters 30 and 30B. This sends rays 32 generally through window 12 to detectors 40 and 40B. The details of the optical coupling will be explained below. These rays give rise to signals in the detector (40, 40B), which is processed by the circuitry 24. The presence of rain drop 34, or other water droplets, mist, or melted snow on outside surface 13 of window 12 alters the strength of the received beams. In a similar fashion to other optical rain sensors, the circuitry 24, preferably also including a microprocessor with suitable software, interprets the change in signal strength as a rain event. Algorithms within the microprocessor determine an appropriate response from the wipers, and a suitable interface and wiper system implements the commands.

In the present invention, the optical paths between emitters (30, 30B) and detectors (40, 40B) vary significantly as the rain sensor is deployed on different window thicknesses. Thus, in a departure from the prior art, operation varies with deployment. The most common deployment, on nominally thick windshield glass, is shown at FIG. 1. In operation, the majority of useful rays are transmitted from emitter to detector in a largely on-axis mode, with certain axis shifts. In detail, rays 92 emanate from the emitter 30, generally traveling toward above-detector collimator lens 52. Rays 92 are deflected by above-emitter collimator lens 52 and largely collimated, and travel through the windshield at about 45 degrees. It can be seen by the slight splay of rays 92 after above-emitter collimator lens 52 that the above-emitter collimator lens 52 is slightly divergent. This slight divergence allows rays 92 to strike a larger area of the receiver side optics group 70 than they would if they were perfectly collimated. Rays 92 are then largely gathered by on-axis receiver lens 72, and focused to a spot on detector die 42. At the window thickness portrayed in the figure, a few of rays 92 also strike above-detector receiver lens 74. Rays 90 may be thought of as functioning in "collimator to focuser mode." That is, they travel generally from collimator region 54 to focuser regions (72, 74) In a converse fashion, rays 90 from the emitter to emitter on-axis lens 50 are largely received by above-detector receiver lens 74. Rays 90 are also slightly divergent, thus striking a significant area of receiver optics group 70. As can be seen from the figure, emitter rays 92 from the on-axis fan inside are directed to the on-axis receiver fan 82 outside. As may be seen from FIG. 1, however, the folder structures (60, 76) also contribute to the operation of the rain sensor in this configuration. Ray 94 from emitter 30 is partially collimated by the emitter-facing lens surface 62, and totally-internally-reflects (TIR's) off emitter-side reflector surface 64. Rays 94 travel through the window at about 45 degrees, and some are ultimately gathered by detector-side on-axis lens 72. These rays are at high obliquity and thus less strong, but nonetheless strike detector 40 and are of some value in sensing rain. Such rays may be thought of as operating in "folder to focuser/collimator to folder" mode. Similarly, and in the same mode some of the rays 90 from the emitter side on-axis lens are captured by receiver folder 76, and usefully directed toward detector die 42. It will be appreciated that the presence of the reflecting structures therefor makes use of a wider fan of rays 32 from emitter 30. Further, the present invention makes greater use of the available extent or acceptance angle of detector 40, gathering a wide detector ray fan 82. In such fashion, the overall efficiency of the rain sensor is increased. Additionally, the folding structures (60, 76) allow for additional useful target regions on the outside surface of the glass.

The operation of the system on a thin (4 mm) window 12 is shown in FIG. 2. The rays (90, 92) through emitter-side collimator region 54 function, for the most part, similarly to that of the more common 6 mm glass deployment of FIG. 1. Because of the thinner glass, on-axis rays 90 do not strike the detector folder 76. Similarly, there is no path from emitter folder 60 to detector on-axis collimator 72. However, the folders (60, 76) aid the operation of the invention in cases where the window is relatively IR energy transmissive, and can thus permit multi-pass or multi-deflection operation. For transmissive windshields, e.g., >65% transmissive to IR, a two-pass ray 100 emanates from emitter 30, is partially collimated (i.e., rays are slightly divergent) by emitter-facing lens 62, reflected by reflecting surface 64, and directed into windshield 12 at about a 45 degree angle. Ray 100 then strikes outside surface 13 of windshield 12, and is reflected back into windshield 12. It then strikes a center region 102 of coupler 16, where it reflects back up into the windshield. After a second pass through windshield 12, two-pass ray 100 is gathered by above-detector receiver lens 74 and focused onto detector die 42. Ray 100 thus forms widely separate target regions that are responsive to the effects of rain. A symmetrical and analogous ray 100D passes through detector-side folder 76 as shown. Thus, the present invention is capable of functioning as a multi-deflection rain sensor, with the associated increase in sensed area, where the characteristics of the glass are suitable.

The present rain sensor invention is shown again on thicker, 8 mm (Recreational Vehicle) glass in FIG. 3. It will be appreciated that the mode of operation of the rain sensor differs significantly from the mode of operation when the rain sensor is deployed on 5 to 6 mm passenger car glass. In deployment of the rain sensor on thicker glasses the more significant portion of the useful emitter rays pass through the folders (60, 76). That is, the "folder to focuser/collimator to folder" mode" dominates the operation of the device. Specifically, rays 106 through emitter folder 60 are transmitted to on-axis receiver lens 72. In a similar and symmetric fashion, rays are transmitted through on-axis collimator lens 50 to detector folder 76. Each of these groups of rays (106, 108) are strong and at relatively low obliquity, and thus are important to the ability of the sensor to detect rain. Still referring to FIG. 3, a ray 104 exists to travel between above-emitter lens 52 and above-detector lens 74, a mode which is absent in the, for example, 4-6 mm glass. Rays 104, however, still contribute to the operation of the rain sensor. Thicker windshields are typically of less IR energy absorptive materials, permitting satisfactory transmittance of the light rays. Additionally, it can be seen from FIG. 3 that the rays form a relatively large sensed area on the outside surface, owing to the differing paths of the rays. Thus, the present rain sensor invention can take advantage of the thicker glass, providing a larger sensed area.

Turning to FIG. 4, deployment of the present invention on very-thick (10 mm) glass, it may be seen that the "collimator to focuser mode" dominates operation of the invention in deployment of the sensor on, for example, 4-6 mm glass are absent. In a fashion similar to deployment on 8 mm glass, a ray 106 is transmitted from emitter 30 to detector 40 by way of emitter folder 60, and on-axis receiver lens 72, in "folder to focuser/collimator to folder mode." Additionally, a ray 110 travels a similar path, but by way of above-detector receiver lens 74. This is possible because of operation of emitter folder 60 i.e., not complete collimation, but slight divergence of some defected rays. On the very-thick glass (10 mm) deployment, a ray 114 also travels from emitter folder 60 to detector folder 76. This mode of operation may be thought of as "folder to folder". These multiple rays result in widely spaced targets, allowing for greater probability of a sensed area being hit by rain drops. The present invention permits operation on very thick glass without the need to adopt a larger, more complex on-axis system, that is, the present invention is exceptionally compact, despite the ability to work with thick windshields. FIG. 4 also shows the virtue of divergent beams at each optical element; rays through the emitter folder 60 splay far enough apart to travel through both of the on-axis and folder structures of the detector side.

The present invention has achieved good performance and compact size by operating in different modes for different thicknesses of glass. For the thinnest windshields, the most important are high obliquity rays, generally directed at 45 degrees towards the inside of the rain sensor. For windshields that exhibit high light transmittance, rays may bounce off the inside surface of the coupler and pass through the windshield twice, further enhancing the sensed surface area. For exceptionally thick windshields, the reflected rays are utilized. These rays are also at fairly high obliquity, but in this case directed at close to 45 degrees to the outside of the rain sensor. At various thicknesses in between, multiple modes of operation are utilized.

As shown in FIGS. 1 through 6, emitter side collimator lens region 54 is preferably made up of two lens surfaces, or lenslets. This arrangement differs from a single Fresnel lens with two segments, in that each of the lens regions is independently optimized. Additionally, each of the sections is allowed to be slightly divergent relative to one another. Were the regions mathematically coupled in a traditional Fresnel design approach, the extent of divergence would be uniform across the entire aperture area. As shown in the present invention, however, each divergent region directs a splay of rays into the windshield. This allows rays from above-emitter collimator lens 52 and the on-axis collimator lens 50 rays to travel toward each other, a situation precluded in normal Fresnel design. This is best illustrated in FIG. 1 (rays 90 and 92). The multi-lens design may be thought of as a "bug-eye" lens approach, where each of the regions does not share a common focal point. The system shown is implemented in just two sections for the predominantly on-axis region. Two lenses were found to be sufficient, but the invention may be implemented with a larger number of lens sections. A beneficial effect of these divergent sections is greater tolerance to misalignment.

It may be appreciated that the optical surfaces of the coupler lenses must all be optimized simultaneously, that is, the above-device and on-axis lenses must function properly for the nominal case mode (6 mm glass), properly directing rays at approximately 45 degrees. These same lenses, however, must also exhibit sufficient efficiency when coupling rays from or to the reflecting structures. Thus, it is necessary in the design of such a system to optimize both modes of operation simultaneously. Recent advances in computational power and optical design software, such as that offered by Zemax, Incorporated, of Tuscon, Ariz., have made such simultaneous optimization possible. In a practical implementation of the invention, a dual-processor computer was set about the task of optimizing all surfaces simultaneously, tracing many trillions of rays over a period of days. The resulting system is thus able to function well in the multiple modes, with differing windshield thickness. FIGS. 1 through 4 presented herein are derived from computer-generated ray tracings, and represent the actual performance of a practical rendition of the invention.

The foregoing discussion discloses and describes exemplary embodiments of the present invention. One skilled in the art will readily recognize from this discussion and from the accompanying drawings and claims, that various changes, modifications and variations can be made therein without departing from the spirit and scope of the invention as defined in the following claims.

What is claimed is:

1. An optical rain sensor for efficiently detecting moisture on a vehicle window having a thickness between 4-12 mm and a corresponding infrared radiation transmission comprising:

an optical coupler into which optical elements are molded, wherein the optical elements comprise a plurality of lens segments for directing infrared rays, and further wherein, the optical coupler is mechanically and optically coupled to a major surface of the vehicle window having a thickness T, and infrared radiation transmittance Tir;

a housing detachably mounted to the coupler;

a circuit board mounted within the housing and being substantially parallel to the vehicle window; and electronic components mounted on the circuit board comprising at least two emitters of infrared radiation each producing rays over a 180° hemisphere substantially normal to the circuit board and at least two detectors of infrared radiation each detecting rays over a 180° hemisphere substantially normal to the circuit board;

the plurality of lens segments being integrally molded into the optical coupler proximate, and at a height above, each of the at least two emitters and at least two detectors, whereby infrared rays emitted from the at least two emitters are collimated, and then directed, nonsequentially, in one or more of at least four optical paths by the plurality of lens segments through the vehicle window and back to the at least two detectors, wherein the specific optical path followed by the infrared radiation is dependent on T and Tir.

2. The optical rain sensor defined in claim 1, wherein T=4.0-6.5 mm, Tir=17-75%, rays useful for sensing moisture are directed, primarily, by at least one: on-axis collimator lens, above-emitter collimator lens, on-axis receiver lens and above-detector receiver lens.

3. The optical rain sensor defined in claim 1, wherein T=6.5-9.5 mm, Tir=20-70%, rays useful for sensing moisture are directed, primarily, by at least one: above-emitter collimator lens and above-detector receiver lens, and emitter-side folder structure and on-axis receiver lens, as well as, on-axis collimator lens and receiver folder structure.

4. The optical rain sensor defined in claim 1, wherein T=9.5-12 mm, Tir=20-65%, rays useful for sensing moisture are directed, primarily by at least one: emitter-side folder structure and detector-side folder structure.

5. The optical rain sensor defined in claim 1, wherein T≦4.0 mm, Tir>70%, rays useful for sensing moisture are directed, primarily, by at least one: on-axis collimator lens and on-axis receiver lens, above-emitter collimator lens and above-detector receiver lens, as well as one or more deflections off a center coupler region.

6. The optical rain sensor defined in claim 1, wherein the optical elements are molded from the group consisting of acrylic and polycarbonate materials.

7. The optical rain sensor defined in claim 1, wherein the infrared rays are collimated by at least one on-axis collimator lens and at least one above-emitter collimator lens.

8. The optical rain sensor defined in claim 1, wherein the at least two emitters comprise a microprocessor which emit rays over a 180° hemisphere.

9. The optical rain sensor defined in claim 1, wherein the at least two detectors comprise one chosen from the group consisting of: a photodiode, a phototransitor, a photovoltaic cell, or a photo-resistor.

10. A moisture sensor for mounting on a first inner surface of a windshield having a thickness T, for detecting water on a plurality of sensing areas on a second outer surface of the windshield, the moisture sensor comprising:

a) a coupler having a mounting surface and an integrally molded multi-functional optical surface, mountable on the first surface of the windshield;

b) a housing detachably secured to the coupler;

c) a planar circuit board secured in the housing and having a device surface which is disposed substantially parallel to the first surface of the windshield;

d) a first emitter for emitting light rays, the first emitter being mounted on the device surface of the circuit board, disposed at a first corner of a square;

e) a second emitter for emitting light rays, the second emitter being mounted on the device surface of the circuit board, disposed at a second corner of the square, opposite the first corner;

f) each of the first and second emitters producing rays over a 180° hemisphere substantially normal to the circuit board having identical emitter groups of optical elements for guiding light rays nonsequentially into the windshield, each emitter group comprising:
 (i) two collimator lenses for collimating light; and
 (ii) two folder lens structures for redirecting light;

g) a first detector mounted on the device surface of the circuit board and disposed at a third corner of the square, for receiving light rays along a first optical path from the first emitter, and for receiving light along a second optical path from the second emitter;

h) a second detector mounted on the device surface of the circuit board and disposed at a fourth corner of the square, for receiving light rays along a third optical path from the first emitter, and for receiving light along a fourth optical path from the second emitter; and i) each of the first and second detectors detecting rays over a 180° hemisphere substantially normal to the circuit board, comprising identical receiver groups of optical elements adjacently disposed, each receiver group being identical in form to the emitter groups, and comprising:

(i) two focuser lenses for focusing light; and
   (ii) two folder structures for receiving light;

wherein, with regard to each of the first, second, third and fourth optical paths, a light beam following one of such paths is dependent on windshield thickness T and the infrared radiation transmittance Tir of the windshield.

11. The moisture sensor defined in claim 10, wherein the sensor operates in one of a plurality of light path modes, wherein the one or more light path modes comprise:

a) collimator lens to focuser lens;
b) collimator lens to folder lens;
c) folder lens to focuser lens; and
d) folder lens to folder lens.

12. The moisture sensor defined in claim 10, wherein the rain sensor is deployed on windshields ranging in thickness T from 4 mm to 12 mm.

13. The moisture sensor defined in claim 10, wherein the optical surface of the coupler is parallel to the first surface of the windshield, and further comprises a folder-to-folder multi-bounce mode of operation.

14. The moisture sensor defined in claim 10, wherein at least 50% of the rays emanating from each of the first and second emitters are directed along an optical path into the windshield at an angle of about 45 degrees with respect to the first windshield surface.

15. The moisture sensor of claim 10, at least 50% of the rays traveling generally toward the detector at an angle of about 45 degrees with respect to the first windshield surface are properly focused onto the detectors.

16. The moisture sensor defined in claim 10, in which the receiver groups of optical elements are symmetrically arranged with respect to the emitter groups of optical elements.

17. The moisture sensor defined in claim 10, in which the coupler is detachable from the housing.

18. The moisture sensor defined in claim 10, in which a) each of the folder of the emitter groups of optical elements further comprises a convex emitter-facing lens; and
b) each of the folders of the receiver groups of optical elements further includes a convex detector-facing lens.

19. The moisture sensor defined in claim 10, in which the collimator lenses comprise segmented lenses, and the focuser lenses comprise segmented lenses.

* * * * *